(12) United States Patent
Li et al.

(10) Patent No.: US 11,364,191 B2
(45) Date of Patent: Jun. 21, 2022

(54) TOPCOAT FOR BASECOAT COMPOSITIONS

(71) Applicant: L'ORÉAL, Paris (FR)

(72) Inventors: Chunhua Li, Hillsborough, NJ (US); Roselin Rosario-Melendez, New York, NY (US); Susan Ashley Desteno, Springfield, NJ (US); Chao Zhu, Berkeley Heights, NJ (US); Rita Jaky El-Khouri, Walnut Creek, CA (US)

(73) Assignee: L'ORÉAL, Paris (FR)

( * ) Notice: Subject to any disclaimer, the term of this patent is extended or adjusted under 35 U.S.C. 154(b) by 112 days.

(21) Appl. No.: 16/553,422

(22) Filed: Aug. 28, 2019

(65) Prior Publication Data
US 2020/0069558 A1    Mar. 5, 2020

Related U.S. Application Data

(60) Provisional application No. 62/725,936, filed on Aug. 31, 2018.

(51) Int. Cl.
| | |
|---|---|
| *A61K 8/898* | (2006.01) |
| *A61Q 1/02* | (2006.01) |
| *A61K 8/891* | (2006.01) |
| *A61K 8/86* | (2006.01) |

(52) U.S. Cl.
CPC ............... *A61K 8/898* (2013.01); *A61K 8/86* (2013.01); *A61K 8/891* (2013.01); *A61Q 1/02* (2013.01)

(58) Field of Classification Search
CPC ... A61K 8/72; A61K 8/81; A61K 8/86; A61K 8/891; A61K 7/021; A61K 8/898; A61Q 1/10
USPC ........................................................ 424/63, 64
See application file for complete search history.

(56) References Cited

U.S. PATENT DOCUMENTS

| | | | |
|---|---|---|---|
| 2011/0117043 A1* | 5/2011 | Dempsey | A61Q 1/10 424/70.7 |
| 2013/0230477 A1* | 9/2013 | Li | A61K 8/8164 424/70.7 |
| 2014/0364394 A1* | 12/2014 | Tamura | A61Q 5/02 514/63 |
| 2018/0360727 A1 | 12/2018 | Lion et al. | |
| 2018/0369123 A1 | 12/2018 | Lion et al. | |

* cited by examiner

*Primary Examiner* — Walter E Webb
(74) *Attorney, Agent, or Firm* — Oblon, McClelland, Maier & Neustadt, L.L.P.

(57) ABSTRACT

The present invention relates to a topcoat composition for basecoat compositions including at least one volatile oil and at least one ethylenic polymer, as well as to systems, kits and methods of treating, making-up and enhancing the appearance of lips, wherein the topcoat composition includes at least one polyamine compound, at least one non-volatile silicone oil and at least one silicone gum.

20 Claims, No Drawings

TOPCOAT FOR BASECOAT COMPOSITIONS

CROSS-REFERENCE TO RELATED APPLICATIONS

This application claims the benefit of priority from U.S. Ser. No. 62/725,936, filed Aug. 31, 2018, the entire contents of which is hereby incorporated by reference.

FIELD OF THE INVENTION

The present invention relates to a topcoat composition for basecoat compositions comprising at least one polyamine compound, at least one non-volatile silicone oil and at least one silicone gum, as well as to systems, kits and methods of treating, making-up and enhancing the appearance of lips, including a basecoat composition comprising at least one volatile oil and at least one ethylenic polymer and the previously-discussed topcoat composition. The topcoat composition does not materially affect the transfer-resistance of the basecoat composition.

DISCUSSION OF THE BACKGROUND

Many cosmetic compositions, including pigmented cosmetics such as lipsticks or lip colors, have been formulated in an attempt to possess long-wearing properties upon application. Unfortunately, many of these compositions do not generally possess both good long-wear/transfer-resistance properties as well as good application properties, good comfort properties and/or good appearance properties (for example, shine properties).

For example, with respect to lip compositions, commercial products containing silicon resins such as MQ resins are known. Such products are known to provide good long wear properties/transfer-resistance. However, such products possess poor application properties and/or poor feel upon application (for example, feels rough).

Typically, a second composition (topcoat) is separately applied to such products to improve poor properties of the compositions to make the products acceptable to consumers. However, topcoat compositions tend to decrease the long-wear/transfer-resistance properties of the lip compositions, thereby rendering the long-wear/transfer resistant composition less acceptable to consumers and less acceptable for their intended purpose.

U.S. Pat. No. 4,731,095 describes copolymers of C22-C28 alpha-olefin, maleic anhydride and 2-ethylhexyl acrylate which react with 1,3-diaminopropane-based polyamines.

U.S. Pat. No. 4,503,182 describes copolymers of C18-C22 alkyl acrylate, maleic anhydride and diisobutylene which react with N-alkylpropylenediamine or N-3-octyloxypropyl-1,3-diaminopropane. The products obtained are used as additive for hydrocarbon distillates such as fuel.

U.S. Pat. No. 5,064,922 describes copolymers of 2-ethylhexyl methacrylate, maleic anhydride and styrene which react with 1-amino-1-methyl-4-aminomethylcyclohexane. The product obtained is used as a binder in paints or inks.

FR 2,583,057 describes copolymers of maleic anhydride, diisobutylene and C16-C22 alkyl (meth)acrylate which react with dimethylaminopropylamine. The product obtained is used as a fuel additive.

WO 2017/108596 and WO 2017/108602 discuss lip composition comprising at least one volatile oil and at least one ethylenic polymer. These references are hereby incorporated by reference in their entirety. However, these references do not disclose topcoat compositions having improved properties.

Thus, there remains a need for improved lip compositions and systems having improved cosmetic properties, particularly good transfer-resistance, feel and shine characteristics upon application.

Accordingly, one aspect of the present invention is a topcoat composition for lip compositions which provide or maintain good cosmetic properties such as, for example, good transfer-resistance, feel and shine properties upon application to a lip composition.

SUMMARY OF THE INVENTION

The present invention relates to a topcoat composition for a basecoat composition comprising at least one volatile oil and at least one ethylenic polymer, wherein the topcoat composition comprises at least one polyamine compound, at least one non-volatile silicone oil and at least one silicone gum. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The present invention relates to kits comprising (1) a basecoat composition comprising at least one volatile oil and at least one ethylenic polymer, and (2) a topcoat composition comprising at least one polyamine compound, at least one non-volatile silicone oil and at least one silicone gum. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The present invention relates to cosmetic systems comprising (1) a basecoat composition comprising at least one volatile oil and at least one ethylenic polymer, and (2) a topcoat composition comprising at least one polyamine compound, at least one non-volatile silicone oil and at least one silicone gum. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The present invention relates to methods for enhancing the appearance of lips comprising applying a basecoat composition comprising at least one volatile oil and at least one ethylenic polymer, and (2) applying a topcoat composition comprising at least one polyamine compound, at least one non-volatile silicone oil and at least one silicone gum. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The present invention relates to methods for making-up lips comprising applying a basecoat composition comprising at least one volatile oil and at least one ethylenic polymer to the lips, and (2) applying a topcoat composition comprising at least one polyamine compound, at least one non-volatile silicone oil and at least one silicone gum to the basecoat composition. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The present invention relates to methods for treating lips comprising (1) applying a basecoat composition comprising at least one volatile oil and at least one ethylenic polymer to the lips, and (2) applying a topcoat composition comprising at least one polyamine compound, at least one non-volatile silicone oil and at least one silicone gum to the basecoat composition. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

It is to be understood that both the foregoing general description and the following detailed description are exemplary and explanatory only, and are not restrictive of the invention.

DETAILED DESCRIPTION OF THE INVENTION

According to the invention, the term "anhydrous" refers to a composition not containing any water, that is to say a composition in which the water that may be present comes only from the water of crystallization or of adsorption of the starting materials. In any case, an anhydrous composition contains less than 5% by weight of water, preferably less than 1% by weight, and better still less than 0.5% by weight of water or 0% by weight of water, relative to the total weight of the composition.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number (e.g. "about 10%" means 9%-11% and "about 2%" means 1.8%-2.2%).

"Film former" or "film forming agent" or "film forming polymer" or "film forming resin" as used herein mean a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Liquid" or "liquid cosmetic" or "liquid lipstick" or "liquid composition" means a composition having a fixed volume, flows to cover the bottom and assumes the shape of the portion of the container it fills and is slightly compressible (as disclosed in General chemistry, Fourth Edition 2005, p. 434

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion and the one far along described.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

"Free of" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of volatile oil" or "devoid of volatile oil" means that volatile oils are preferably omitted (that is 0% by weight), but can be present in the composition at an amount of less than about 0.25% by weight, typically less than about 0.1% by weight, typically less than about 0.05% by weight, based on the total weight of the composition as a whole. And, for example, "free of hydrocarbon oil" or "devoid of hydrocarbon oil" means that hydrocarbon oils are preferably omitted (that is 0% by weight), but can be present in the composition at an amount of less than about 0.25% by weight, typically less than about 0.1% by weight, typically less than about 0.05% by weight, based on the total weight of the composition as a whole. Also, for example, "free of wax" or "devoid of wax" means that waxes are preferably omitted (that is 0% by weight), but can be present in the composition at an amount of less than about 0.25% by weight, typically less than about 0.1% by weight, typically less than about 0.05% by weight, based on the total weight of the composition as a whole.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

As used herein a range of ratios is meant to include every specific ratio within, and combination of subranges between the given ranges.

"Keratinous materials" includes materials containing keratin such as hair, skin, eyebrows, lips and nails.

"Volatile", as used herein, means having a flash point of less than about 100° C.

"Non-volatile", as used herein, means having a flash point of greater than about 100° C.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

The compositions and methods of the present invention can comprise, consist of, or consist essentially of the essential elements and limitations of the invention described herein, as well as any additional or optional ingredients, components, or limitations described herein or otherwise useful.

Basecoat Composition

According to preferred embodiments of the present invention, a basecoat composition comprising at least one volatile oil and at least one ethylenic polymer is provided. Suitable compositions are described, for example, in PCT patent application publication no. WO 2017/108602, the entire contents of which is hereby incorporated by reference.

Volatile Oil

According to preferred embodiments, the basecoat compositions of the present invention comprise at least one volatile oil.

The expression "volatile oil" means any non-aqueous medium capable of evaporating on contact with the skin or the lips in less than one hour at room temperature and atmospheric pressure.

Examples of suitable volatile oils include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile oil may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |

TABLE 2-continued

| Compound | Flash Point (° C.) | Viscosity (cSt) |
|---|---|---|
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 cSt) from Dow Corning | 102 | 3 |

The at least one volatile oil is preferably present in the basecoat compositions of the present invention in an amount ranging from about 5% to about 75% by weight, preferably from about 10% to about 60% by weight, and preferably from about 15% to about 50% by weight, including all ranges and subranges therebetween, all weights being based on the weight of the composition as a whole.

Ethylenic Polymer

According to preferred embodiments, the basecoat compositions of the present invention comprise at least one ethylenic polymer.

According to preferred embodiments, the ethylenic polymer is derived from polymerization of:

(a) 45% to 95% by weight, relative to the total weight of monomers, of an ethylenic monomer bearing an at least $C_8$ linear or branched alkyl group;

(b) 5% to 25% by weight of maleic anhydride; and (c) 0 to 50% by weight of additional monomer chosen from:

(i) polydimethylsiloxane silicone monomers bearing a mono(meth)acryloyloxy end group as defined below; and (ii) linear or branched $C_1$-$C_6$ alkyl (meth)acrylate or $C_6$-$C_{12}$ cycloalkyl (meth)acrylate non-silicone monomers.

According to preferred embodiments, the ethylenic polymer comprises an ethylenic monomer bearing an at least $C_8$ linear or branched alkyl group (referred to as a fatty-chain ethylenic monomer); the alkyl group may be a linear or branched $C_8$-$C_{22}$ or $C_8$ to $C_{12}$ alkyl group.

Such a fatty-chain ethylenic monomer may be chosen from:

a) linear or branched $C_8$-$C_{22}$ alkyl (meth)acrylates (i.e. comprising a $C_8$-$C_{22}$ alkyl group);

b) the (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;

c) the vinyl esters of formula $R_5$—CO—O—CH=$CH_2$ in which $R_5$ represents a linear or branched $C_8$-$C_{22}$ alkyl group;

d) the ethers of formula $R_6$—O—CH=$CH_2$ in which $R_6$ represents a linear or branched $C_8$-$C_{22}$ alkyl group.

Linear or branched $C_8$-$C_{22}$ alkyl groups that may be mentioned include octyl, 2-ethylhexyl, isooctyl, nonyl, decyl, undecyl, lauryl, myristyl, palmityl, stearyl, eicosyl and behenyl radicals, and especially a 2-ethylhexyl, lauryl, behenyl or stearyl group.

Preferably, the fatty-chain ethylenic monomer is chosen from $C_8$-$C_{22}$ and especially $C_8$-$C_{18}$ alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, 2-ethylhexyl methacrylate, stearyl acrylate or stearyl methacrylate is preferably used.

2-Ethylhexyl acrylate is preferentially used.

The fatty-chain monomer may be present in said ethylenic polymer in a content ranging from 45% to 90% by weight and preferably ranging from 50% to 90% by weight, relative to the total weight of monomers, including all ranges and subranges therebetween.

In the absence of additional monomer in the ethylenic polymer, the fatty-chain monomer may be present in a content ranging from 75% to 95% by weight, preferably ranging from 75% to 90% by weight and preferentially ranging from 78% to 87% by weight, relative to the total weight of monomers, including all ranges and subranges therebetween.

In the presence of additional monomer in the ethylenic polymer, the fatty-chain monomer may be present in a content ranging from 45% to 94.5% by weight, preferably ranging from 45% to 90% by weight, preferentially ranging from 50% to 75% by weight and more preferentially ranging from 52% to 67% by weight, relative to the total weight of monomers, including all ranges and subranges therebetween.

The ethylenic polymer used according to the invention contains maleic anhydride.

According to preferred embodiments, maleic anhydride is present in the ethylenic polymer in a content ranging from 10% to 25% by weight and preferably ranging from 13% to 22% by weight, relative to the total weight of monomers, including all ranges and subranges therebetween.

According to preferred embodiments, the additional silicone monomer, if present, is a polydimethylsiloxane bearing a mono(meth)acryloyloxy end group of formula (I) (referred to hereinbelow as a silicone monomer) below:

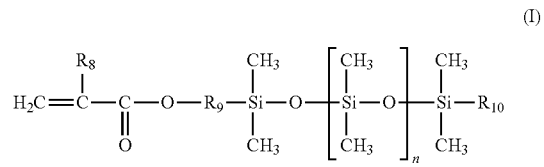

(I)

in which:

$R_8$ denotes a hydrogen atom or a methyl group; preferably methyl;

$R_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;

$R_{10}$ denotes a linear or branched alkyl group containing from 1 to 10 carbon atoms, especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc. or the silicone macromonomers sold under the names X-22-2475, X-22-2426 and X-22-174DX by Shin-Etsu.

The additional silicone monomer, if present, may be present in the ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight, including all ranges and subranges therebetween.

The additional non-silicone monomer chosen from linear or branched $CrC_6$ alkyl (meth)acrylates, if present, may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate. Methyl (meth)acrylate or ethyl (meth)acrylate is preferably used.

The $C_6$-$C_{12}$ cycloalkyl (meth)acrylate is preferably isobornyl (meth)acrylate.

The additional non-silicone monomer, if present, may be present in said ethylenic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight, including all ranges and subranges therebetween.

According to one embodiment of the invention, the ethylenic polymer does not comprise any additional monomer: it is formed from ethylenic monomer bearing an at least $C_8$ linear or branched alkyl group and maleic anhydride.

According to another embodiment of the invention, the ethylenic polymer comprises at least one additional monomer as defined previously. The additional monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight, including all ranges and subranges therebetween.

According to another embodiment of the invention, the ethylenic polymer comprises at least one additional silicone monomer as defined previously.

According to another embodiment of the invention, the ethylenic polymer comprises at least one additional non-silicone monomer as defined previously. Preferably, it is a $C_6$-$C_{12}$ cycloalkyl (meth)acrylate.

According to another embodiment of the invention, the ethylenic polymer comprises at least one additional silicone monomer and at least one additional non-silicone monomer as defined previously.

According to a first embodiment of the invention, the ethylenic polymer comprises, or consists of:
(a) 75% to 95% by weight, relative to the total weight of monomers, of linear or branched $C_8$-$C_{22}$ alkyl (meth)acrylate;
(b) 5% to 25% by weight of maleic anhydride.

The ethylenic polymer preferably comprises, or consists of:
(a) 75% to 95% by weight, relative to the total weight of monomers, of linear or branched $C_8$-$C_{18}$ alkyl (meth)acrylate;
(b) 5% to 25% by weight of maleic anhydride.

In particular, the ethylenic polymer comprises, or consists of:
(a) 75% to 95% by weight, relative to the total weight of monomers, of 2-ethylhexyl (meth)acrylate;
(b) 5% to 25% by weight of maleic anhydride.

In particular, the ethylenic polymer comprises, or consists of:
(a) 75% to 95% by weight, relative to the total weight of monomers, of stearyl (meth)acrylate;
(b) 5% to 25% by weight of maleic anhydride.

In particular, the ethylenic polymer comprises, or consists of:
(a) 75% to 95% by weight, relative to the total weight of monomers, of a mixture of 2-ethylhexyl (meth)acrylate and of stearyl (meth)acrylate;
(b) 5% to 25% by weight of maleic anhydride.

Preferably, the ethylenic polymer comprises, or consists of:
(a) 75% to 90% by weight, relative to the total weight of monomers, of linear or branched $C_8$-$C_{22}$ alkyl (meth)acrylate;
(b) 10% to 25% by weight of maleic anhydride.

The ethylenic polymer preferably comprises, or consists of:
(a) 75% to 90% by weight, relative to the total weight of monomers, of linear or branched $C_8$-$C_{18}$ alkyl (meth)acrylate;
(b) 10% to 25% by weight of maleic anhydride.

In particular, the ethylenic polymer comprises, or consists of:
(a) 75% to 90% by weight, relative to the total weight of monomers, of 2-ethylhexyl (meth)acrylate;
(b) 10% to 25% by weight of maleic anhydride.

In particular, the ethylenic polymer comprises, or consists of:
(a) 75% to 90% by weight, relative to the total weight of monomers, of stearyl (meth)acrylate;
(b) 10% to 25% by weight of maleic anhydride.

In particular, the ethylenic polymer comprises, or consists of:
(a) 75% to 90% by weight, relative to the total weight of monomers, of a mixture of 2-ethylhexyl (meth)acrylate and of stearyl (meth)acrylate;
(b) 10% to 25% by weight of maleic anhydride.

Preferentially, the ethylenic polymer comprises, or consists of:
(a) 78% to 87% by weight, relative to the total weight of monomers, of linear or branched $C_8$-$C_{22}$ alkyl (meth)acrylate;
(b) 13% to 22% by weight of maleic anhydride.

The ethylenic polymer especially comprises, or consists of:
(a) 78% to 87% by weight, relative to the total weight of monomers, of linear or branched $C_8$-$C_{18}$ alkyl (meth)acrylate;
(b) 13% to 22% by weight of maleic anhydride.

In particular, the ethylenic polymer comprises, or consists of:
(a) 78% to 87% by weight, relative to the total weight of monomers, of 2-ethylhexyl (meth)acrylate;
(b) 13% to 22% by weight of maleic anhydride.

In particular, the ethylenic polymer comprises, or consists of:
(a) 78% to 87% by weight, relative to the total weight of monomers, of stearyl (meth)acrylate;
(b) 13% to 22% by weight of maleic anhydride.

In particular, the ethylenic polymer comprises, or consists of:
(a) 78% to 87% by weight, relative to the total weight of monomers, of a mixture of 2-ethylhexyl (meth)acrylate and of stearyl (meth)acrylate;
(b) 13% to 22% by weight of maleic anhydride.

The ethylenic polymer may be chosen from the following copolymers:

2-ethylhexyl acrylate/maleic anhydride (85/15 by weight);

2-ethylhexyl acrylate/maleic anhydride (80/20 by weight);

2-ethylhexyl acrylate/stearyl acrylate/maleic anhydride (50/30/20 by weight).

According to preferred embodiments, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of silicone monomer (I) as described previously.

The ethylenic polymer preferably comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of silicone monomer (I) as described previously.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of silicone monomer (I) as described previously.

The ethylenic polymer preferably comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of silicone monomer (I) as described previously.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of silicone monomer (I) as described previously.

The ethylenic polymer preferably comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of silicone monomer (I) as described previously.

Preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of silicone monomer (I) as described previously.

The ethylenic polymer preferably comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of silicone monomer (I) as described previously.

The ethylenic polymer may be chosen from the following copolymers:
2-ethylhexyl acrylate/maleic anhydride/silicone monomer (I);
stearyl acrylate/maleic anhydride/silicone monomer (I);
2-ethylhexyl acrylate/stearyl acrylate/maleic anhydride/silicone monomer (I);
in the respective monomer contents described previously, and in particular: the 2-ethylhexyl acrylate/PDMS methacrylate/maleic anhydride copolymer (50/30/20 by weight).

According to preferred embodiments, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of additional non-silicone monomer chosen from linear or branched $C_1$-$C_6$ alkyl (meth)acrylates or $C_6$-$Ci_2$ cycloalkyl (meth)acrylates.

The ethylenic polymer preferably comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of $C_6$-$Ci_2$ cycloalkyl (meth)acrylate.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of isobornyl (meth)acrylate.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of additional non-silicone monomer chosen from linear or branched $C_1$-$C_6$ alkyl (meth)acrylates or $C_6$-$C_{12}$ cycloalkyl (meth)acrylates.

The ethylenic polymer preferably comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of $C_6$-$C_{12}$ cycloalkyl (meth)acrylate.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of isobornyl (meth)acrylate.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of additional non-silicone monomer chosen from linear or branched $C_1$-$C_6$ alkyl (meth)acrylates or $C_6$-$C_{12}$ cycloalkyl (meth)acrylates.

The ethylenic polymer preferably comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;

(c) 15% to 40% by weight of $C_6$-$C_{12}$ cycloalkyl (meth)acrylate.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of isobornyl (meth)acrylate.

More preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of additional non-silicone monomer chosen from linear or branched $C_1$-$C_6$ alkyl (meth)acrylates or $C_6$-$C_{12}$ cycloalkyl (meth)acrylates.

The ethylenic polymer preferably comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of $C_6$-$C_{12}$ cycloalkyl (meth)acrylate.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of isobornyl (meth)acrylate.

The ethylenic polymer may be chosen from the following copolymers:
2-ethylhexyl acrylate/maleic anhydride/isobornyl (meth)acrylate;
stearyl acrylate/maleic anhydride/isobornyl (meth)acrylate;
2-ethylhexyl acrylate/stearyl acrylate/maleic anhydride/isobornyl (meth)acrylate;
in the respective monomer contents described previously.

According to preferred embodiments, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of a mixture of additional non-silicone monomer chosen from $C_6$-$C_{12}$ cycloalkyl (meth)acrylates and of silicone monomer (I) as described previously.

The ethylenic polymer preferably comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of a mixture of $C_6$-$C_{12}$ cycloalkyl (meth)acrylate and of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of a mixture of isobornyl (meth)acrylate and of silicone monomer (I) as described previously.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of a mixture of additional non-silicone monomer chosen from linear or branched $C_1$-$C_6$ alkyl (meth)acrylates or $C_6$-$C_{12}$ cycloalkyl (meth)acrylates and of silicone monomer (I) as described previously.

The ethylenic polymer preferably comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of a mixture of $C_6$-$C_{12}$ cycloalkyl (meth)acrylate and of silicone monomer (I) as described previously.

In particular, the ethylenic polymer comprises, or consists of:

(a) 45% to 90% by weight, relative to the total weight of monomers, of 2-ethylhexyl (meth)acrylate;

(b) 5% to 25% by weight of maleic anhydride;

(c) 5% to 50% by weight of a mixture of isobornyl (meth)acrylate and of silicone monomer (I) as described previously.

In particular, the ethylenic polymer comprises, or consists of:

(a) 45% to 90% by weight, relative to the total weight of monomers, of stearyl (meth)acrylate;

(b) 5% to 25% by weight of maleic anhydride;

(c) 5% to 50% by weight of a mixture of isobornyl (meth)acrylate and of silicone monomer (I) as described previously.

In particular, the ethylenic polymer comprises, or consists of:

(a) 45% to 90% by weight, relative to the total weight of monomers, of a mixture of 2-ethylhexyl (meth)acrylate and of stearyl (meth)acrylate;

(b) 5% to 25% by weight of maleic anhydride;

(c) 5% to 50% by weight of a mixture of isobornyl (meth)acrylate and of silicone monomer (I) as described previously.

Preferentially, the ethylenic polymer comprises, or consists of:

(a) 50% to 75% by weight, relative to the total weight of monomers, of linear or branched $C_8$-$C_{22}$ alkyl (meth)acrylate;

(b) 10% to 25% by weight of maleic anhydride;

(c) 15% to 40% by weight of a mixture of additional non-silicone monomer chosen from linear or branched $C_1$-$C_6$ alkyl (meth)acrylates or $C_6$-$C_{12}$ cycloalkyl (meth) acrylates and of silicone monomer (I) as described previously.

The ethylenic polymer preferably comprises, or consists of:

(a) 50% to 75% by weight, relative to the total weight of monomers, of linear or branched $C_8$-$C_{18}$ alkyl (meth)acrylate;

(b) 10% to 25% by weight of maleic anhydride;

(c) 15% to 40% by weight of a mixture of $C_6$-$C_{12}$ cycloalkyl (meth)acrylate and of silicone monomer (I) as described previously.

In particular, the ethylenic polymer comprises, or consists of:

(a) 50% to 75% by weight, relative to the total weight of monomers, of 2-ethylhexyl (meth)acrylate;

(b) 10% to 25% by weight of maleic anhydride;

(c) 15% to 40% by weight of a mixture of isobornyl (meth)acrylate and of silicone monomer (I) as described previously.

In particular, the ethylenic polymer comprises, or consists of:

(a) 50% to 75% by weight, relative to the total weight of monomers, of stearyl (meth)acrylate;

(b) 10% to 25% by weight of maleic anhydride;

(c) 15% to 40% by weight of a mixture of isobornyl (meth)acrylate and of silicone monomer (I) as described previously.

In particular, the ethylenic polymer comprises, or consists of:

(a) 50% to 75% by weight, relative to the total weight of monomers, of a mixture of 2-ethylhexyl (meth)acrylate and of stearyl (meth)acrylate;

(b) 10% to 25% by weight of maleic anhydride;

(c) 15% to 40% by weight of a mixture of isobornyl (meth)acrylate and of silicone monomer (I) as described previously.

Preferentially, the ethylenic polymer comprises, or consists of:

(a) 52% to 67% by weight, relative to the total weight of monomers, of linear or branched $C_8$-$C_{22}$ alkyl (meth)acrylate;

(b) 13% to 22% by weight of maleic anhydride;

(c) 20% to 35% by weight of a mixture of additional non-silicone monomer chosen from linear or branched $C_1$-$C_6$ alkyl (meth) acrylates or $C_6$-$C_{12}$ cycloalkyl (meth) acrylates and of silicone monomer (I) as described previously.

The ethylenic polymer preferably comprises, or consists of:

(a) 52% to 67% by weight, relative to the total weight of monomers, of linear or branched $C_8$-$C_{18}$ alkyl (meth)acrylate;

(b) 13% to 22% by weight of maleic anhydride;

(c) 20% to 35% by weight of a mixture of $C_6$-$C_{12}$ cycloalkyl (meth)acrylate and of silicone monomer (I) as described previously.

In particular, the ethylenic polymer comprises, or consists of:

(a) 52% to 67% by weight, relative to the total weight of monomers, of 2-ethylhexyl (meth)acrylate;

(b) 13% to 22% by weight of maleic anhydride;

(c) 20% to 35% by weight of a mixture of isobornyl (meth)acrylate and of silicone monomer (I) as described previously.

In particular, the ethylenic polymer comprises, or consists of:

(a) 52% to 67% by weight, relative to the total weight of monomers, of stearyl (meth)acrylate;

(b) 13% to 22% by weight of maleic anhydride;

(c) 20% to 35% by weight of a mixture of isobornyl (meth)acrylate and of silicone monomer (I) as described previously.

In particular, the ethylenic polymer comprises, or consists of:

(a) 52% to 67% by weight, relative to the total weight of monomers, of a mixture of 2-ethylhexyl (meth)acrylate and of stearyl (meth)acrylate;

(b) 13% to 22% by weight of maleic anhydride;

(c) 20% to 35% by weight of a mixture of isobornyl (meth)acrylate and of silicone monomer (I) as described previously.

The ethylenic polymer may be chosen from the following copolymers:

2-ethylhexyl acrylate/maleic anhydride/isobornyl (meth) acrylate/silicone monomer (I);

stearyl acrylate/maleic anhydride/isobornyl (meth)acrylate/silicone monomer (I);

2-ethylhexyl acrylate/stearyl acrylate/maleic anhydride/ isobornyl (meth)acrylate/silicone monomer (I);

in the respective monomer contents described previously.

Preferably, the ethylenic polymer used according to the invention consists of the monomers described previously.

Preferably, the ethylenic polymer used according to the invention is nonionic.

Preferably, the ethylenic polymer used according to the invention has a weight-average molecular weight ranging from 5000 to 1 000 000 g/mol, preferably ranging from 8000 to 500 000 g/mol and preferentially ranging from 10 000 to 350 000 g/mol, including all ranges and subranges therebetween.

The molecular weight may be determined by steric exclusion chromatography, with THF eluent, polystyrene standard, 2414 refractometric detector from Waters.

The ethylenic polymer may be a random, alternating (block) or gradient polymer. Preferably, the polymer is random.

The ethylenic polymer may be prepared by radical polymerization of the monomers described previously, preferably as a mixture or added sequentially during the polymerization, preferably using an organic solvent with a boiling point of greater than or equal to 60° C., for instance isododecane, ethanol, ethyl acetate, tetrahydrofuran, methyltetrahydrofuran or methyl ethyl ketone. The organic solvent makes it possible to dissolve the monomers used and the polymer formed.

The polymerization is preferably performed in the presence of a radical initiator especially of peroxide type (for example tert-butyl peroxy-2-ethylhexanoate: Trigonox 21 S; 2,5-dimethyl-2,5-bis(2-ethylhexanoylperoxy)hexane: Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The polymerization may be performed at a temperature ranging from 60 to 100° C., and preferably ranging from 60 to 85° C. The polymerization time may be about 24 hours.

The at least one ethylenic polymer is preferably present in the basecoat compositions of the present invention in an amount ranging from about 0.1% to about 40% by weight, preferably from about 0.5% to about 35% by weight, preferably from about 1% to about 30% by weight, and preferably from about 10% to about 30% by weight, including all ranges and subranges therebetween, all weights being based on the weight of the composition as a whole.

Topcoat Composition

According to the present invention, topcoat compositions comprising at least one polyamine compound, at least one non-volatile silicone oil, and at least one silicone gum are provided. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

Polyamine Compound

According to preferred embodiments, the topcoat composition of the present invention comprises at least one polyamine compound.

According to preferred embodiments, the polyamine compound is a compound bearing several primary amine and/or secondary amine groups or alternatively amino alkoxysilanes. It may thus be chosen from amino alkoxysilane compounds, diamine compounds and triamine compounds.

According to preferred embodiments, the polyamine compound is a compound comprising from 2 to 20 carbon atoms, in particular a non-polymeric compound. The term "non-polymeric compound" means a compound which is not directly obtained via a monomer polymerization reaction Suitable polyamine compounds include, for example, N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine. Preferably, the polyamine compound is chosen from ethylenediamine, 1,3-propylenediamine and 1,4-butylenediamine. Preferentially, the polyamine compound is ethylenediamine.

According to preferred embodiments, the polyamine compound may be chosen from amino alkoxysilanes, such as those of formula (II):

$$R'_1Si(OR'_2)_z(R'_3)_x \qquad (II)$$

in which:
R'$_1$ is a linear or branched, saturated or unsaturated, cyclic or acyclic $C_1$-$C_6$ hydrocarbon-based chain substituted with a group chosen from the following groups:
amine $NH_2$ or NHR with R=$C_1$-$C_4$ alkyl,
an aryl or aryloxy group substituted with an amino group or with a C $C_4$ aminoalkyl group,
R'1 possibly being interrupted in its chain with a heteroatom (O, S, NH) or a carbonyl group (CO), R'i being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

Preferably, R'$_2$ represents an alkyl group comprising from 1 to 4 carbon atoms.

Preferably, R'$_2$ represents a linear alkyl group, comprising from 1 to 4 carbon atoms.

Preferably, R'$_2$ represents an ethyl group.

Preferably, R'$_3$ represents an alkyl group comprising from 1 to 4 carbon atoms.

Preferably, R'$_3$ represents a linear alkyl group, comprising from 1 to 4 carbon atoms.

Preferably, R'$_3$ represents a methyl or ethyl group.

Preferably, R'$_1$ is an acyclic chain.

Preferably, R'$_1$ is a linear or branched, saturated or unsaturated $C_1$-$C_6$ hydrocarbon-based chain, substituted with an amine group $NH_2$ or NHR (R=Cr$C_6$ alkyl, $C_3$-$C_6$ cycloalkyl or $C_6$ aromatic). Preferentially, R'i is a saturated linear $C_1$-$C_6$ hydrocarbon-based chain substituted with an amine group $NH_2$. More preferentially, R'$_1$ is a saturated linear $C_2$-$C_4$ hydrocarbon-based chain substituted with an amine group $NH_2$.

Preferably, R'$_1$ is a saturated linear $C_1$-$C_6$ hydrocarbon-based chain substituted with an amine group $NH_2$.

R'$_2$ represents an alkyl group comprising from 1 to 4 carbon atoms,

R'$_3$ represents an alkyl group comprising from 1 to 4 carbon atoms,

Preferably, z is equal to 3.

Preferably, the amino alkoxysilane of formula (II) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

Preferably, the amino alkoxysilane (II) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the amino alkoxysilane (II) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine and lysine.

Preferentially, the amine compound is chosen from ethylenediamine, 1,3-propylenediamine, 1,4-butylenediamine and 3-aminopropyltriethoxysilane (APTES). More preferentially, the amine compound is ethylenediamine or 3-aminopropyltriethoxysilane (APTES).

The polyamine compound may also be chosen from amine-based polymers, preferably having a weight-average molecular weight ranging from 500 to 1 000 000, preferably ranging from 500 to 500 000, and preferentially ranging from 500 to 100 000, including all ranges and subranges therebetween.

Suitable amine-based polymers include, for example, poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing $NH_2$ groups, such as polylysine, for example the product sold by the company JNC Corporation (formerly Chisso); aminodextran, such as the product sold by the company CarboMer Inc.; amino polyvinyl alcohol, such as the product sold by the company CarboMer Inc., acrylamidopropylamine-based copolymers; chitosans; polydimethylsiloxanes comprising primary amine groups at the chain end or on side chains, for example aminopropyl side or end groups, for instance those of formula (A) or (B) or (C):

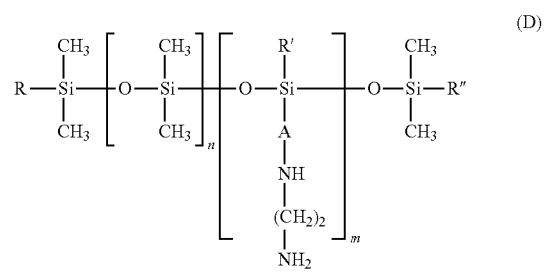

In formula (A): the value of n is such that the weight-average molecular weight of the silicone is between 500 and 55 000. As an example of aminosilicone (A), mention may be made of those sold under the names DMS-A11, DMS-A12, DMS-A15, DMS-A21, DMS-A31, DMS-A32 and DMS-A35 by the company Gelest.

In formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest.

In formula (C), the value of n is such that the weight-average molecular weight of the silicone is between 500 and 3000. As an example of silicone (C), mention may be made of those sold under the names MCR-A11 and MCR-A12 by the company Gelest.

Suitable polymers also include amodimethicones of formula (D):

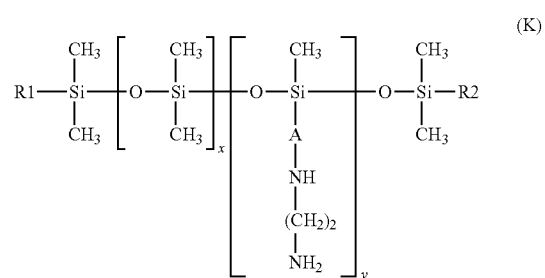

in which R, R' and R", which may be identical or different, each represent a $C_i$-$C_4$ alkyl or hydroxyl group, A represents a $C_3$ alkylene group and m and n are such that the weight-average molecular mass of the compound is between 5000 and 500 000 approximately;

Suitable polymers also include the amodimethicones of formula (K):

(K)

in which:
R1 and R2, which may be identical or different, preferably identical, represent a linear or branched, saturated or unsaturated alkyl group comprising from 6 to 30 carbon atoms, preferably from 8 to 24 carbon atoms and preferentially from 12 to 20 carbon atoms,
A represents a linear or branched alkylene radical group containing from 2 to 8 carbon atoms,
x and y are numbers ranging from 1 to 5000; preferably, x ranges from 10 to 2000 and preferably from 100 to 1000; preferably, y ranges from 1 to 100.

Preferably, A comprises from 3 to 6 carbon atoms, in particular 4 carbon atoms; preferably, A is branched. A may be a divalent radical chosen from: —$CH_2CH_2CH_2$— and —$CH_2CH(CH_3)CH_2$—.

Preferably, R1 and R2, which may be identical or different, represent a saturated linear alkyl group comprising from 6 to 30 carbon atoms, preferentially from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

Preferentially, for the amodimethicone of formula (K):
x ranges from 10 to 2000 and especially from 100 to 1000;
y ranges from 1 to 100;
A comprises from 3 to 6 carbon atoms, and in particular 4 carbon atoms; preferably, A is branched; preferentially, A is chosen from the divalent radicals:
—CH2CH2CH2- and
—CH$_2$CH(CH$_3$)CH$_2$—; and
R1 and R2, which may be identical or different, represent a saturated linear radical comprising from 6 to 30 carbon atoms, preferably from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

A preferred amodimethicone of formula (K) is, for example, bis-cetearyl amodimethicone (INCI name), such as the product sold under the name Silsoft® AX by the company Momentive Performance Materials.

Suitable polymers include polyether amines such as those sold under the reference Jeffamine® from the company Huntsman; and especially:

Polyethylene glycol and/or polypropylene glycol α,ω-diamines (bearing an amine function at the end of the chain), which may comprise from 2 to 80 units derived from propylene oxide, or which may comprise from 2 to 50 units derived from ethylene oxide and from 1 to 10 units derived from propylene oxide, for instance the products sold under the names Jeffamine® D-230, D-400, D-2000, D-4000, ED-600, ED-9000, ED-2003;

Polytetrahydrofuran (or polytetramethylene glycol) α,ω-diamines;

polybutadiene α,ω-diamines;

Polyamidoamine (PANAM) dendrimers bearing amine end functions;

Poly(meth)acrylates or poly(meth)acrylamides bearing primary or secondary amine side functions, such as poly(3-aminopropyl)methacrylamide or poly(2-aminoethyl) methacrylate.

Suitable amine-based polymers include polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from polydimethylsiloxanes comprising primary amine groups at the chain end or on side chains, amodimethicones of formula (K), in particular bis-cetearyl amodimethicone; polyethylene glycol and/or polypropylene glycol α,ω-diamines; ethylenediamine, 1,3-propylenediamine, 1,4-butylenediamine, preferably ethylenediamine.

Preferentially, the amine compounds used in the process according to the invention are chosen from polydimethylsiloxanes comprising aminopropyl end groups at the chain end, bis-cetearyl amodimethicone, polyethylene glycol/polypropylene glycol α,ω-diamine copolymers comprising from 2 to 50 units derived from ethylene oxide and from 1 to 10 units derived from propylene oxide, 3-aminopropyltriethoxysilane (APTES).

When the compound is an amino alkoxysilane, the composition containing it is anhydrous.

Preferably, the polyamine compound is used in a mole ratio of amine group of the amine compound/maleic anhydride group of the ethylenic polymer in the basecoat composition ranging from 0.01 to 10, preferably ranging from 0.1 to 5, preferentially ranging from 0.1 to 2 and preferentially ranging from 0.1 to 1, including all ranges and subranges therebetween.

On contact with the ethylenic polymer in the basecoat composition, the polyamine compound reacts with the maleic anhydride functions to form a crosslinked polymer, for example in the following manner:

Scheme I

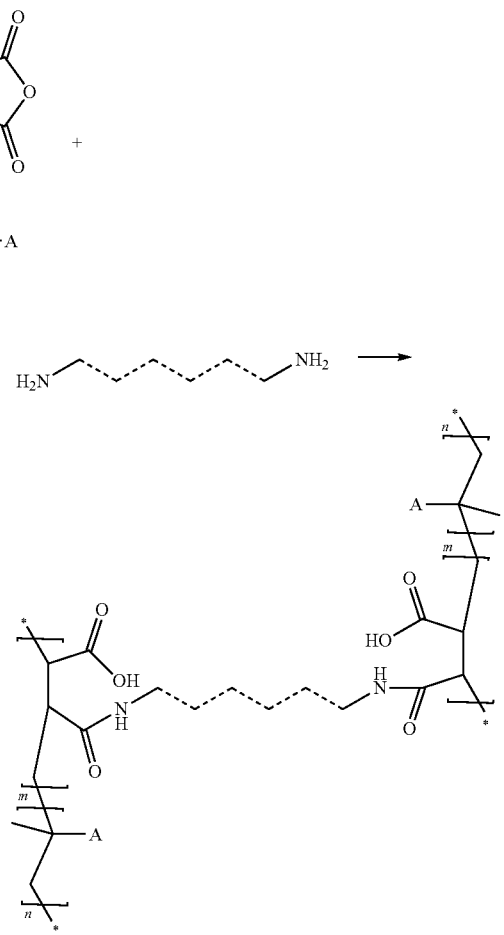

the unit bearing the group A symbolizing the unit derived from the fatty-chain ethylenic monomer.

The crosslinked polymer may thus be obtained by reacting said polyamine compound with the maleic anhydride acrylic polymer described previously. Some or all of the anhydride groups react with the NH or NH$_2$ group of the amine compound and form a unit bearing an amide group and a carboxylic acid group as described in scheme I.

The amino alkoxysilane (II) used in anhydrous medium reacts with the maleic anhydride group present in the polymer to form a unit having the following formula:

Scheme II

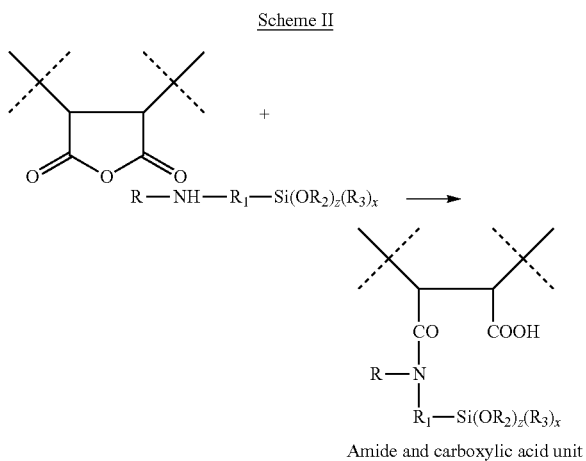

Amide and carboxylic acid unit

The polymer bearing an amino alkoxysilane group may thus be obtained by reacting in anhydrous medium the amino alkoxysilane (II) with the maleic anhydride ethylenic polymer described previously. Some or all of the anhydride groups react with the NH group of compound (II) and form a unit bearing an amide group and a carboxylic acid group as described in scheme II.

The at least one polyamine compound is preferably present in the topcoat compositions of the present invention in an amount ranging from about 5% to about 75% by weight, preferably from about 20% to about 70% by weight, preferably from about 30% to about 65% by weight, and preferably from about 40% to about 60% by weight, including all ranges and subranges therebetween, all weights being based on the weight of the composition as a whole.

Non-Volatile Silicone Oil

According to preferred embodiments, the topcoat composition of the present invention comprises at least one non-volatile silicone oil. Volatility of oils can be determined using the evaporation speed as set forth in U.S. Pat. No. 6,338,839, the content of which is herein incorporated by reference.

Non-volatile oils include low viscosity oils (preferably having a viscosity from about 5 cSt to about 50,000 cSt, preferably from about 10 cSt to about 10,000 cSt, preferably from about 100 cSt to about 5,000 cSt, and preferably from about 500 cSt to about 2,500 cSt, including all ranges and subranges therebetween) and high viscosity oils (preferably having a viscosity of from about 100,000 cSt to about 750,000 cSt, preferably from about 200,000 cSt to about 600,000 cSt, and preferably from about 250,000 cSt to about 500,000 cSt, including all ranges and subranges therebetween, and mixtures thereof. In contrast to waxes, oils are liquids at room temperature.

Suitable silicone oils are described, for example in US 2011/0293550 and US 2004/0126350, both of which are herein incorporated by reference. Non-limiting examples of suitable non-volatile silicone oils include polydimethylsiloxanes (PDMS) (CTFA designation "dimethicones"), such compounds optionally comprising alkyl or alkoxy groups which are pendent or at the end of a silicone chain, these groups containing from 2 to 24 carbon atoms; polydiethyl siloxanes; and phenylated silicone oils.

Suitable non-volatile phenylated silicone oils include, for example, linear or branched non-volatile polydimethylsiloxanes (PDMS) comprising phenyl groups which are pendent or at the end of the silicone chain.

Suitable examples include, but are not limited to, phenyl trimethicones, such as phenyl trimethylsiloxy trisiloxane sold under the reference Dow Corning 556 Cosmetic Grade Fluid, phenyl dimethicones, phenyl trimethylsiloxy diphenylsiloxanes, diphenyl dimethicones, diphenyl methyldiphenyl trisiloxanes, 2-phenylethyl trimethylsiloxysilicates, trimethyl pentaphenyl trisiloxane, such as the silicone oil sold by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane), and trimethyl siloxyphenyl dimethicones, such as the product sold under the reference Belsil PDM 1000 by the company Wacker.

Preferably, non-volatile silicone oil is present in the topcoat compositions of the present invention in an amount ranging from about 10% to about 85% by weight, preferably from about 20% to about 80% by weight, and preferably from about 25% to about 75% by weight, including all ranges and subranges therebetween, all weights based on the weight of the composition as a whole.

Silicone Gum

According to preferred embodiments, the topcoat composition of the present invention comprises at least one silicone gum.

According to preferred embodiments, the silicone gum corresponds to the formula:

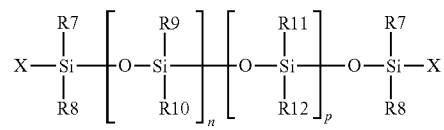

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of from about 900,000 cSt to about 50,000,000 cSt, preferably from about 950,000 cSt to about 25,000,000 cSt, and preferably from about 1,000,000 cSt to about 10,000,000 cSt, including all ranges and subranges therebetween.

In general, n and p can each take values ranging from 0 to 10,000, such as from 0 to 5,000.

Among the silicone gums which can be used according to the invention, mention may be made of those for which:

the substituents $R_7$ to $R_{12}$ and X represent a methyl group, p=0 and n=2 700, such as the product sold or made under the name SE30 by the company General Electric, the substituents $R_7$ to $R_{12}$ and X represent a methyl group, p=0 and n=2 300, such as the product sold or made under the name AK 500 000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents $R_7$ to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhône-Poulenc (Rhodia Chimie).

In preferred embodiments, the silicone gum correspond to the following formula:

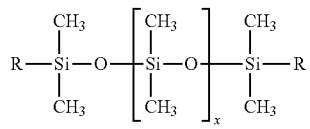

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, and mixtures thereof. The silicone gums employed in the present invention may be terminated by triorganosilyl groups of the formula $R'_3$ where R' is a radical of monovalent hydrocarbons containing from 1 to 6 carbon atoms, hydroxyl groups, alkoxyl groups and mixtures thereof.

In preferred embodiments, at least one silicone gum present in the topcoat composition is a dimethiconol.

Preferably, silicone gum oil is present in the topcoat compositions of the present invention in an amount ranging from about 0.5% to about 25% by weight, from about 1% to about 20% by weight, from about 3% to 17% by weight, and preferably from about 5% to about 15% by weight, including all ranges and subranges therebetween, all weights based on the weight of the composition as a whole.

Preferably, more non-volatile silicone oil is present in the compositions of the present invention than silicone gum, preferably in a non-volatile silicone oil to silicone gum weight ratio of about 2.5:1 to about 10:1, preferably from about 3:1 to about 9:1, and preferably from about 4:1 to about 8:1, including all ranges and subranges therebetween.

Additional Ingredients

According to preferred embodiments, the basecoat composition, the topcoat composition, or both can comprise additional ingredients typically included in cosmetic compositions. A non-exhaustive discussion of such ingredients is set forth below.

Film-Forming Agents

According to preferred embodiments, the topcoat composition further comprises as least one film-forming agent, the basecoat composition comprises a film-forming agent, or both. Preferably, if a film-forming agent is present in the topcoat and/or basecoat composition, the film-forming agent is preferably a silicone film-forming agent selected from the group consisting of silicone resins, polyorganosiloxane copolymers, and mixtures thereof. Also preferably, the silicone resin is selected from the group consisting of siloxysilicate resins, silsesquioxane resins, and mixtures thereof.

Wax

According to preferred embodiments, the topcoat and/or basecoat compositions of the present invention may optionally comprise at least one wax. For the purposes of the present invention, a wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes can generally be those used in cosmetics. The waxes may be of natural origin, for instance beeswax, carnauba wax, candelilla wax, ouricoury wax, Japan wax, cork fiber wax, sugar cane wax, paraffin wax, lignite wax, microcrystalline waxes, lanolin wax, montan wax, ozokerites and hydrogenated oils, for instance hydrogenated jojoba oil.

The waxes also may be of synthetic origin, for instance polyethylene waxes derived from the polymerization of ethylene, waxes obtained by Fischer-Tropsch synthesis, esters of fatty acids and of glycerides that are solid at 40° C.

Particular waxes include, for example, polyethylene waxes, for example the product sold under the name Performalene 500-L Polyethylene (New Phase Technology), and polymethylene waxes, for instance the product sold under the name Cirebelle 303 (Sasol).

Particular waxes include, for example, silicone waxes such as polypropylsilsesquioxane wax substituted with alkyl units having at least 30 carbons. Polypropylsilsesquioxane waxes, in general, have been disclosed in patent publication WO2005/100444 and U.S. Pat. No. 8,586,013, the entire contents of which are hereby incorporated by reference in their entirety. A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax.

Preferably, if present, wax is present in the topcoat compositions of the present invention in an amount ranging from about 1% to about 30% by weight, from about 3% to about 25% by weight, from about 4% to 40% by weight, and preferably from about 5% to about 15% by weight, including all ranges and subranges therebetween, all weights based on the weight of the composition as a whole.

Pigments

The lip and/or topcoat compositions of the present invention may optionally further comprise at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742);

ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 15%, from about 1.5% to about 12%, and from about 2% to about 10%, based on the weight of the composition.

Filler

The lip and/or topcoat compositions of the present invention may optionally further comprise at least one filler. Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

Volatile Oil

According to the present invention, the topcoat composition may optionally further comprise at least one volatile oil. The suitable "volatile oils" identified above in connection with basecoat compositions of the present invention may also be used in connection with the topcoat compositions of the present invention. However, as noted above, preferably the topcoat compositions of the present invention do not comprise volatile oil.

If present in the topcoat compositions of the present invention, the at least one volatile oil is preferably present in the topcoat compositions of the present invention in an amount ranging from about 5% to about 75% by weight, preferably from about 10% to about 60% by weight, and preferably from about 15% to about 50% by weight, including all ranges and subranges therebetween, all weights being based on the weight of the composition as a whole.

Additional Additives

The compositions of the present invention may optionally further comprise at least one cosmetically or dermatologically acceptable additive such as thickener, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

According to preferred embodiments, kits comprising (1) a basecoat composition comprising at least one volatile oil and at least one ethylenic polymer, and (2) a topcoat composition comprising at least one polyamine compound, at least one non-volatile silicone oil and at least one silicone gum are provided. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

According to preferred embodiments, cosmetic systems comprising (1) a basecoat composition comprising at least one volatile oil and at least one ethylenic polymer, and (2) a topcoat composition comprising at least one polyamine compound, at least one non-volatile silicone oil and at least one silicone gum are provided. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

According to preferred embodiments, methods for enhancing the appearance of lips comprising applying a basecoat composition comprising at least one volatile oil and at least one ethylenic polymer to the lips, and (2) applying a topcoat composition comprising at least one polyamine compound, at least one non-volatile silicone oil and at least one silicone gum to the basecoat composition are provided. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

According to preferred embodiments, methods for making-up lips comprising applying a basecoat composition comprising at least one volatile oil and at least one ethylenic polymer to the lips, and (2) applying a topcoat composition comprising at least one polyamine compound, at least one non-volatile silicone oil and at least one silicone gum to the basecoat composition are provided. Preferably, "making up" the lips includes applying at least one coloring agent to the lips in an amount sufficient to provide color to the lips. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

According to preferred embodiments, methods for treating lips comprising applying a basecoat composition comprising at least one volatile oil and at least one ethylenic polymer to the lips, and (2) applying a topcoat composition comprising at least one polyamine compound, at least one non-volatile silicone oil and at least one silicone gum to the basecoat composition are provided. Preferably, the topcoat composition consists essentially of at least one polyamine compound, at least one non-volatile silicone oil and at least one silicone gum. Preferably, the topcoat composition does not comprise hydrocarbon oil. Preferably, the topcoat composition does not comprise wax. Preferably, the topcoat composition does not comprise volatile oil. Preferably, when the topcoat composition is applied to the basecoat composition, the topcoat composition does not inhibit the transfer-resistance of the basecoat composition.

The compositions and methods of the present invention can "comprise," "consist of" or "consist essentially of" the identified ingredients and process steps. For purposes of the compositions and methods of the present invention where the invention "consists essentially of" the identified ingredients and/or process steps, the sole "basic and novel property" of such compositions and/or methods is transfer-resistance. Further, given that it is contemplated that other transfer-resistance enhancers or boosters (for example, additional film-forming agents) can be added to the invention methods and compositions in the context of the present invention, a "material effect" on the basic and novel property of the invention can only be an adverse effect. That is, because positive effects on transfer-resistance properties (such as those effected by additional film-forming agents) are within the scope of the present invention, only ingredients which have a material adverse effect on transfer-resistance properties would be relevant to determining whether or not compositions or methods "consist essentially of" the required elements.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The present invention will be better understood from the examples which follow. The examples are intended to be nonrestrictive and explanatory only, with the scope of the invention defined by the claims.

Example 1—Topcoat Compositions

The following tables set forth exemplary topcoat compositions of the present invention and comparative compositions.

| Ingredient | Topcoat Composition 4 | Topcoat Composition 5 | Comparative Topcoat Commercial Product* |
|---|---|---|---|
| Poly(dimethylsiloxane), bis(3-aminopropyl) terminated | 50 | 50 | |
| Isododecane | 50 | 0 | |
| Dimethiconol Gum | 0 | 3.75 | |
| Dimethicone Gum | 0 | 5 | |
| Dimethicone Fluid | 0 | 41.25 | |

Example 2—Exemplary Basecoat Compositions

| RM Name | Basecoat composition 1 | Basecoat composition 2 | Comparative Basecoat composition Commercial Product Containing MQ resin** |
|---|---|---|---|
| Maleic Anhydride Copolymer in Isododecane (39% Active) | 64.1 | 75.95 | |
| Pigment | 6 | 6 | |
| Isododecane | QS | QS | |

Commercial Topcoat*: TRIMETHYL PENTAPHENYL TRISILOXANE, IS-DIGLYCERYL POLYACYLADIPATE-2, OZOKERITE, CERA ALBA/BEESWAX/CIRE DABEILLE, CALCIUM SODIUM BOROSILICATE, CALCIUM ALUMINUM BOROSILICATE, TOCOPHERYL ACETATE, PARFUM/FRAGRANCE. [+/−MAY CONTAIN/PEUT CONTENIR MICA, CI 77891/TITANIUM DIOXIDE, CI 77491/IRON OXIDES] F.I.L. D8974/11.

Commercial Basecoat composition**: ISODODECANE, TRIMETHYLSILOXYSILICATE, NYLON-611/DIMETHICONE COPOLYMER, DISTEARDIMONIUM HECTORITE, LAUROYL LYSINE, C30-45 ALKYLDIMETH- YLSILYL POLYPROPYLSILSESQUIOXANE, ALUMINA, PROPYLENE CARBONATE, SYNTHETIC FLUORPHLOGOPITE, SILICA, CALCIUM SODIUM BOROSILICATE, CALCIUM ALUMINUM BOROSILICATE, POLYETHYLENE TEREPHTHALATE, PARFUM/FRAGRANCE, ALUMINUM HYDROXIDE, ACRYLATES COPOLYMER, BENZYL ALCOHOL, DIMETHICONE, PARAFFIN, TIN OXIDE. [+/−MAY CONTAIN/PEUT CONTENIR MICA, CI 77891/TITANIUM DIOXIDE, CI 77491, CI 77492, CI 77499/IRON OXIDES, CI 15850/RED 7, CI 15985/YELLOW 6 LAKE, CI 45410/RED 28 LAKE, CI 45380/RED 22 LAKE, CI 19140/YELLOW 5 LAKE, CI 42090/BLUE 1 LAKE, CI 75470/CARMINE]F.I.L. D41008/5.

Example 3—Exemplary Method of Preparing Invention Composition(s)

All formulas were prepared using a high speed mixer.
Basecoat Formula: To a high speed mixer cup the Maleic anhydride copolymer, pre-dispersed pigments within isododecane, and the QS isododecane were added. The sample was sealed with the appropriate high speed mixed lid, and mixed in the high speed mixer at 2750 RPM for 2 minutes.
Topcoat Formula: To a high speed mixer cup the Poly (dimethylsiloxane), bis(3-aminopropyl) terminated, and remaining ingredients were added. The sample was sealed with the appropriate high speed mixed lid, and mixed in the high speed mixer at 2750 RPM for two minutes. After two minutes the sample was checked for homogeneity, and if the sample was not homogenous that sample was mixed for an additional two minutes at 2750 RPM. This continued until the sample was completely homogenous.

Example 4—Evaluation Methods and Test Results

Oil Abrasion Test
Formulas were casted on polypropylene abrasion cards using a 1 mil wet drawdown bar on top of a hotplate which was set at 33° C. For all samples, first the basecoat formula was casted, and post application the film was allowed to dry for 2-4 hours at 33° C. and 60% RH. Following this dry time period, an additional topcoat film was applied on top using a 1 mil wet drawdown bar on top of a hotplate set at 33° C. The film was additionally dried overnight at 33° C. and 60% RH. In the instance where topcoat was not used, the sample was just additionally dried at 33° C. and 60% RH overnight without the addition of the topcoat.
Once the film was set, an olive oil soaked sponge was dabbed across the sample and the olive oil was allowed to soak the film for 30 minutes. The olive oil soaked sponge was first hydrated with milli-Q water and then placed into a bath of olive oil prior to use. After the 30 minutes was completed, the film was light wiped with a kimwipe and then ready for abrasion. The film was taped down on a drawdown machine (Gardco Drawdown Machine), equipped with a metal bar that could made contact directly on top of the film. To the metal bar, two pieces of loop side of Velcro was adhered so that the loop side of Velcro made direct contact to the film. The metal bar equipped with the Velcro pieces was moved across the film in the forward and then backwards direction. One run was considered one full forward and back crossing across the film. When the sample became fully removed was when the value depicted in the table below. Therefore a lower number means that the sample was removed at a lower number of passes across the film, while a high value means a high number of passes were required to achieve removal. Samples were only tested until 50 strokes, therefore in some instances even at 50 there was still sample remaining.

| Product | Oil-Abrasion Test Results |
|---|---|
| Basecoat composition 2 (alone) | 5 |
| Basecoat composition 1 + Topcoat Composition 4 | 50 (±0.0) |
| Basecoat composition 1 + Topcoat Composition 5 | 50 (±0.0) |
| Commercial Basecoat composition (alone) | 32.5 (±3.54) |
| Commercial Basecoat composition + Commercial Topcoat Composition | 25 (±0.0) |

Samples using Basecoat composition 1+Topcoat Composition 4 and Basecoat composition 1+Topcoat Composition 5 outperformed the Comparative samples and combinations of comparatives, with improved high shine values and low tack values. Moreover the inclusion of non-volatiles (Basecoat composition 1+Topcoat Composition 4) resulted in a more comfortable product.

What is claimed is:
1. A cosmetic system comprising (1) a basecoat composition comprising at least one volatile oil and at least one ethylenic polymer, and (2) an anhydrous topcoat composition comprising at least one polyamine compound, at least one non-volatile silicone oil and at least one silicone gum, wherein the ethylenic polymer is derived from polymerization of monomers comprising maleic anhydride.
2. The cosmetic system of claim 1, wherein the topcoat composition consists essentially of at least one polyamine compound, at least one non-volatile silicone oil and at least one silicone gum.
3. A kit comprising (1) a basecoat composition comprising at least one volatile oil and at least one ethylenic polymer, and (2) an anhydrous topcoat composition comprising at least one polyamine compound, at least one non-volatile silicone oil and at least one silicone gum, wherein the ethylenic polymer is derived from polymerization of monomers comprising maleic anhydride.
4. The kit of claim 3, wherein the topcoat composition consists essentially of at least one polyamine compound, at least one non-volatile silicone oil and at least one silicone gum.
5. A method for making-up lips comprising applying a basecoat composition comprising at least one volatile oil and at least one ethylenic polymer to the lips, and applying an anhydrous topcoat composition comprising at least one polyamine compound, at least one non-volatile silicone oil and at least one silicone gum to the basecoat composition, wherein the ethylenic polymer is derived from polymerization of monomers comprising maleic anhydride.
6. The method of claim 5, wherein the topcoat composition consists essentially of at least one polyamine compound, at least one non-volatile silicone oil and at least one silicone gum to the basecoat composition.
7. The method of claim 5, wherein when the topcoat composition is applied to the basecoat composition, the topcoat composition does not inhibit the transfer-resistance of the basecoat composition.
8. The method of claim 6, wherein when the topcoat composition is applied to the basecoat composition, the topcoat composition does not inhibit the transfer-resistance of the basecoat composition.
9. The cosmetic system of claim 1, wherein the ethylenic polymer is derived from polymerization of:

(a) 45% to 95% by weight, relative to the total weight of monomers, of an ethylenic monomer bearing an at least C8 linear or branched alkyl group;
(b) 5% to 25% by weight of maleic anhydride; and
(c) 0 to 50% by weight of at least one additional monomer selected from the group consisting of:
(i) polydimethylsiloxane silicone monomers bearing a mono(meth)acryloyloxy end group; and
(ii) linear or branched $C_1$-$C_6$ alkyl (meth)acrylate or $C_6$-$C_{12}$ cycloalkyl (meth)acrylate non-silicone monomers.

10. The method of claim 6, wherein the ethylenic polymer is derived from polymerization of:
(a) 45% to 95% by weight, relative to the total weight of monomers, of an ethylenic monomer bearing an at least C8 linear or branched alkyl group;
(b) 5% to 25% by weight of maleic anhydride; and
(c) 0 to 50% by weight of at least one additional monomer selected from the group consisting of:
(i) polydimethylsiloxane silicone monomers bearing a mono(meth)acryloyloxy end group; and
(ii) linear or branched $C_1$-$C_6$ alkyl (meth)acrylate or $C_6$-$C_{12}$ cycloalkyl (meth)acrylate non-silicone monomers.

11. The method of claim 7, wherein the ethylenic polymer is derived from polymerization of:
(a) 45% to 95% by weight, relative to the total weight of monomers, of an ethylenic monomer bearing an at least C8 linear or branched alkyl group;
(b) 5% to 25% by weight of maleic anhydride; and
(c) 0 to 50% by weight of at least one additional monomer selected from the group consisting of:
(i) polydimethylsiloxane silicone monomers bearing a mono(meth)acryloyloxy end group; and
(ii) linear or branched $C_1$-$C_6$ alkyl (meth)acrylate or $C_6$-$C_{12}$ cycloalkyl (meth)acrylate non-silicone monomers.

12. The method of claim 8, wherein the ethylenic polymer is derived from polymerization of:
(a) 45% to 95% by weight, relative to the total weight of monomers, of an ethylenic monomer bearing an at least C8 linear or branched alkyl group;
(b) 5% to 25% by weight of maleic anhydride; and
(c) 0 to 50% by weight of at least one additional monomer selected from the group consisting of:
(i) polydimethylsiloxane silicone monomers bearing a mono(meth)acryloyloxy end group; and
(ii) linear or branched $C_1$-$C_6$ alkyl (meth)acrylate or $C_6$-$C_{12}$ cycloalkyl (meth)acrylate non-silicone monomers.

13. The system of claim 9, wherein the ethylenic polymer comprises an ethylenic monomer bearing a linear or branched $C_8$-$C_{22}$ alkyl group.

14. The system of claim 1, wherein maleic anhydride is present in the ethylenic polymer in a content ranging from 10% to 25% by weight of the ethylenic polymer.

15. The cosmetic system of claim 1, wherein the polyamine compound is selected from amino alkoxysilanes of formula (II):

$$R'_1Si(OR'_2)_z(R'_3)_x \quad \text{(II)}$$

in which:
R'$_1$ is a linear or branched, saturated or unsaturated, cyclic or acyclic C1-C6 hydrocarbon-based chain substituted with a group selected from the following groups:
amine NH$_2$ or NHR with R=$C_1$-$C_4$ alkyl,
an aryl or aryloxy group substituted with an amino group or with a $C_1$-$C_4$ aminoalkyl group,
with R'1 optionally containing in its chain a heteroatom or a carbonyl group,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

16. The cosmetic system of claim 1, wherein the polyamine compound is a polydimethylsiloxane comprising primary amine groups at least one chain end or on side chains.

17. The cosmetic system of claim 1, wherein the polyamine compound is a polydimethylsiloxane comprising aminopropyl end groups at the chain end.

18. The cosmetic system of claim 1, wherein the polyamine compound is selected from the group consisting of polydimethylsiloxanes comprising primary amine groups at least one the chain end or on side chains, amodimethicones, polyethylene glycol α,ω-diamines, polypropylene glycol α,ω-diamines, ethylenediamine, 1,3-propylenediamine, 1,4-butylenediamine, and mixtures thereof.

19. The cosmetic system of claim 1, wherein the polyamine compound is selected from the group consisting of polydimethylsiloxanes comprising aminopropyl end groups at the chain end, bis-cetearyl amodimethicone, polyethylene glycol/polypropylene glycol α,ω-diamines copolymers comprising from 2 to 50 units derived from ethylene oxide and from 1 to 10 units derived from propylene oxide, 3-aminopropyltriethoxysilane (APTES), and mixtures thereof.

20. The kit of claim 3, wherein the ethylenic polymer is derived from polymerization of:
(a) 45% to 95% by weight, relative to the total weight of monomers, of an ethylenic monomer bearing an at least C8 linear or branched alkyl group;
(b) 5% to 25% by weight of maleic anhydride; and
(c) 0 to 50% by weight of at least one additional monomer selected from the group consisting of:
(i) polydimethylsiloxane silicone monomers bearing a mono(meth)acryloyloxy end group; and
(ii) linear or branched $C_1$-$C_6$ alkyl (meth)acrylate or $C_6$-$C_{12}$ cycloalkyl (meth)acrylate non-silicone monomers.

* * * * *